United States Patent
Yli-Koski et al.

(10) Patent No.: US 9,354,173 B2
(45) Date of Patent: May 31, 2016

(54) MICROTITER PLATE READER APPARATUS AND DYNAMIC FILTER STORAGE

(75) Inventors: Antero Yli-Koski, Piikkio (FI); Pauli Salmelainen, Masku (FI); Jukka Valtonen, Lieto (FI)

(73) Assignee: Labrox Oy, Turku (FI)

(*) Notice: Subject to any disclaimer, the term of this patent is extended or adjusted under 35 U.S.C. 154(b) by 588 days.

(21) Appl. No.: 13/593,485

(22) Filed: Aug. 23, 2012

(65) Prior Publication Data

US 2013/0050705 A1    Feb. 28, 2013

(30) Foreign Application Priority Data

Aug. 24, 2011 (FI) ...................................... 20115822

(51) Int. Cl.
*G01N 21/00* (2006.01)
*G01N 21/64* (2006.01)
*G01J 1/04* (2006.01)

(52) U.S. Cl.
CPC ........... *G01N 21/6445* (2013.01); *G01J 1/0444* (2013.01); *G01J 1/0488* (2013.01); *G01J 1/0492* (2013.01); *G01N 21/645* (2013.01); *G01N 21/6408* (2013.01)

(58) Field of Classification Search
CPC .................... G01N 21/6452; G01N 2021/6439
USPC .......... 250/227.22, 205, 458.1, 226; 356/432, 356/300, 239.1, 394–418
See application file for complete search history.

(56) References Cited

U.S. PATENT DOCUMENTS

| | | |
|---|---|---|
| 4,076,420 A | 2/1978 | De Maeyer et al. |
| 4,977,325 A | 12/1990 | Bowen |
| 6,042,785 A | 3/2000 | Harju |
| 6,097,025 A * | 8/2000 | Modlin ................ G01N 21/253 250/205 |
| 6,790,652 B1 | 9/2004 | Terry |

(Continued)

FOREIGN PATENT DOCUMENTS

| | | |
|---|---|---|
| CA | 1138221 A2 | 12/1982 |
| DE | 19702754 A1 | 7/1988 |
| EP | 0981043 A1 | 2/2000 |
| EP | 1598686 A2 | 11/2005 |
| WO | 2005066981 A1 | 7/2005 |

OTHER PUBLICATIONS

G.Schmidtke et al SOL-ACES: Autocalibrating EUV/UV spectrometers for measurements onboard the International Space Station. Advances in Space Research 2006, vol. 37, pp. 273-282 whole document.

(Continued)

*Primary Examiner* — Kara E Geisel
*Assistant Examiner* — Iyabo S Alli
(74) *Attorney, Agent, or Firm* — Ziegler IP Law Group, LLC (57) ABSTRACT

An apparatus for optically measuring samples, including a radiation source configured to form an excitation beam in an excitation channel, a detector configured to detect an emission beam in an emission channel and a filter configured to be located, in an excitation position, in the excitation channel, and in an emission position, in the emission channel. The apparatus further includes a first filter storage comprising a first set of filter storage positions, a second filter storage comprising a second set of filter storage positions, and a filter transfer mechanism configured to move the filter between the excitation position, the emission position, the first set of filter storage positions and the second set of filter storage positions.

20 Claims, 3 Drawing Sheets

(56) References Cited

U.S. PATENT DOCUMENTS

| | | | |
|---|---|---|---|
| 7,265,833 B2 * | 9/2007 | Oldham | B82Y 10/00 356/344 |
| 2003/0042428 A1 | 3/2003 | Peukert et al. | |
| 2003/0117628 A1 | 6/2003 | Harju et al. | |
| 2003/0127609 A1 | 7/2003 | El-hage et al. | |
| 2003/0229270 A1 | 12/2003 | Suzuki et al. | |
| 2004/0264647 A1 | 12/2004 | Graf | |
| 2005/0111090 A1 | 5/2005 | Kleinteich et al. | |
| 2007/0117158 A1 | 5/2007 | Coumans | |

OTHER PUBLICATIONS

Sutter Instrument Company. Lambda 10-3 Optical Filter Changer and SmartShutter Control System Operation Manual Retrieved on Nov. 29, 2012. http://www.sutter.com/manuals/LB10-3_OpMan.pdf>,pp. 19-21.

International Search Report, PCT/FI2012/050799, mailed Dec. 27, 2012.

Extended European Search Report, Application No. 12825483.6-1554/2748586 PCT/FI2012050799, mailed Jun. 10, 2015 (10 pages).

* cited by examiner

MICROTITER PLATE READER APPARATUS AND DYNAMIC FILTER STORAGE

TECHNICAL FIELD

The present invention generally relates to an apparatus of a microtiter plate reader. The invention relates particularly, though not exclusively, to dynamic storing of filters for the microtiter plate reader.

BACKGROUND ART

Presently, microtiter plate readers with separate filter slides for excitation filters and emission filters are known. Apparatuses for irradiating samples which can be characterized by light penetrating the samples (transmission), the light reflected by the samples (reflection), light initiated on or in the sample (fluorescence) or light emitted by the samples themselves (luminescence) have long been known as microscopes, spectrophotometers, fluorometers and the like. The light that penetrates the sample during the irradiation or is reflected by the same or the fluorescence initiated on or in the sample will be designated below as "light originating from the sample" and will be measured for example by one or several photodetectors. The use of different optical filters for influencing light rays with which the samples are radiated or light that is transmitted through the same (so-called excitation filters) is known. Similarly, emission filters are known which influence the light emitted by the samples. Especially user-friendly are filter slides which comprise at least one such filter, but preferably several such optical filters, which can be moved with a defined movement into the beam path.

SUMMARY

According to a first example aspect of the invention there is provided an apparatus comprising:
 a radiation source configured to form an excitation beam in an excitation channel;
 a detector configured to detect an emission beam in an emission channel;
 a filter configured to be located, in an excitation position, in the excitation channel, and in an emission position, in the emission channel; and
 a filter module for storing and moving the filter between a storage position, the excitation position and the emission position;
 the filter module comprising:
  a first filter storage comprising a first set of filter storage positions;
  a second filter storage comprising a second set of filter storage positions; and
  a filter transfer mechanism configured to move the filter between the excitation position, the emission position, the first set of filter storage positions and the second set of filter storage positions.

The apparatus may be configured to store an association between optical information of the filter and a position of the filter, wherein the position of the filter being at least one of the following: the excitation position, the emission position, the first set of filter storage positions and the second set of filter storage positions. Furthermore, the movement of the filter caused by the filter transfer mechanism may be detected and the association between the optical information of the filter and the position of the filter may be updated.

In an embodiment, information on filters to a user of the apparatus is provided and the user is provided an option to select the filter for at least one of the following: the excitation position and the emission position. The filter may be moved, using the filter transfer mechanism, between the excitation position, the emission position, the first set of filter storage positions and the second set of filter storage positions, based on the user's selection.

The first filter storage and the second filter storage may be positioned at least partially on the excitation channel and the emission channel, respectively. The excitation position may be configured to be a filter storage position of the first filter storage and the emission position may be configured to be a filter storage position of the second filter storage. The second filter storage may be configured to store an exchange filter position and the filter transfer mechanism may be further configured to move the filter between the exchange filter position and the first set of filter storage positions. The first filter storage and the second filter storage are round-shaped or slide-shaped, for example. The first filter storage and the second filter storage may be configured to be movable compared to the radiation source and the detector.

In an embodiment, the first filter storage is positioned next to the second filter storage. Furthermore, at least one of the first set of filter storage positions and the second set of first filter storage positions comprises an aperture configured to provide a focal point to the measured sample. Still furthermore, at least two filter storage positions comprise apertures of different sizes configured to provide alternative focal points to the measured sample. The apparatus may further comprise a microtiter plate reader and the measured samples may be on a microtiter plate. The sample is measured, for example, utilizing at least one of the following technologies:
 fluorescence intensity;
 absorbance;
 luminescence;
 time resolved fluorescence; and
 fluorescence polarization.

According to a second example aspect there is provided a method comprising:
 providing a first set of filter storage positions in a first filter storage;
 providing a second set of filter storage positions in a second filter storage;
 moving the excitation filter and the emission filter between the excitation position, the emission position, the first set of filter storage positions and the second set of filter storage positions
 forming an excitation beam in an excitation channel using a radiation source;
 filtering the excitation beam in the excitation channel using an excitation filter located in an excitation position;
 filtering an emission beam in the emission channel using an emission filter located in an emission position; and
 detecting the emission beam in an emission channel using a detector.

According to a third example aspect there is provided a computer program embodied on a computer readable medium comprising computer executable program code which, when executed by at least one processor of an apparatus, causes the apparatus to perform the method of the second example aspect.

According to a fourth example aspect there is provided a filter module for storing and moving a filter between a storage position, an excitation position and an emission position, wherein the filter module comprising:
 a first filter storage comprising a first set of filter storage positions;

a second filter storage comprising a second set of filter storage positions; and a filter transfer mechanism configured to move the filter between the excitation position, the emission position, the first set of filter storage positions and the second set of filter storage positions.

Different non-binding example aspects and embodiments of the present invention have been illustrated in the foregoing. The above embodiments are used merely to explain selected aspects or steps that may be utilized in implementations of the present invention. Some embodiments may be presented only with reference to certain example aspects of the invention. It should be appreciated that corresponding embodiments may apply to other example aspects as well.

BRIEF DESCRIPTION OF THE DRAWINGS

The invention will be described, by way of example only, with reference to the accompanying drawings, in which.

DETAILED DESCRIPTION

In the following description, like numbers denote like elements.

An apparatus of a microtiter plate reader uses a set of filters used for excitation and emission. In an embodiment of the invention, the apparatus comprises at least one storage for the filters and a mechanism to move the filters between the storage and the operating positions for the excitation and the emission. Furthermore, a computer system for controlling the filter operation and exchange is provided. A user of the apparatus may be provided a list of filters in the storage with their optical characteristics, and based on the user's selections the computer system may control the mechanism to operate the desired filters for the excitation and the emission.

In an embodiment, the filter is an optical filter operating on a band around a certain center wavelength of radiation, for example light. Furthermore, high-pass and low-pass filters may be used. The optical filter may be an interference filter, a colored glass filter or a combination of both, for example. An excitation filter may be used for bandpassing a certain center wavelength band from the excitation radiation of a sample. An emission filter may be used for bandpassing a certain center wavelength band from the emission radiation of a sample.

In an embodiment, the apparatus comprises a filter storage configured to store both excitation filters and emission filters. Such filter storage may comprise two filter storages for storing the filters and a filter transfer mechanism for moving the filters between the two storages. At least one position in the first filter storage may be configured to be an excitation position overlapping at least partially an excitation channel of the apparatus. At least one position in the second filter storage may be configured to be an emission position overlapping at least partially an emission channel of the apparatus. The filter transfer mechanism is configured to move filters also from the excitation position to the emission position, and vice versa, using the two filter storages. The apparatus may further comprise an exchange position, through which filters may be added and removed from the filter storage. The computer system of the apparatus may control the addition and removal of filters to the storage and keeps track of exact positions of filters in the storage.

Figure 1:
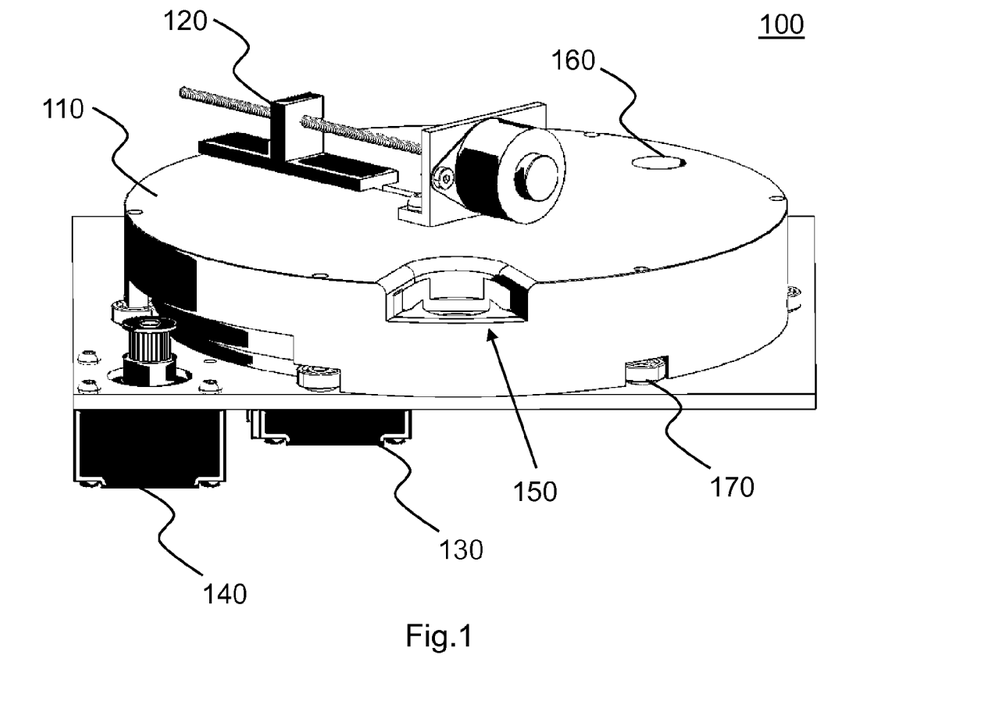
FIG. 1 shows a schematic picture of a filter module an apparatus according to an example embodiment of the invention.

FIG. 1 shows a schematic picture of a filter module 100 of an apparatus according to an example embodiment of the invention. In this example, the apparatus is a microtiter plate reader. In FIG. 1 the filter module 100 of the apparatus is shown in normal operating position. The filter module 100 comprises at least one cover part 110 covering at least partially a first and a second filter storage (not shown). The filter module 100 may further comprise a filter transfer mechanism 120 for transferring filters in the storage and to/from the storage. The filter module 100 may further comprise a motor 130 for moving the first filter storage and a motor 140 for moving the second filter storage. The motors may move the filter storages for example using a belt or a gearwheel. Furthermore, an exchange aperture 150 is provided in the cover part 110. Using the exchange aperture 150, a user of the apparatus may insert and remove filters to/from the filter storage of the filter module 100. The cover part 110 may also comprise at least one beam aperture 160 for allowing a radiation beam to pass through at least partially the filter storage of the filter module 100. The radiation beam may be for example an excitation beam or an emission beam for measuring a sample of a microtiter plate. The filter storage of the filter module 100 may thus at least partially overlap an excitation channel for the excitation beam or an emission channel for the emission beam. Rollers or running wheels 170 may be used to assist in moving and driving the filter storages.

Figure 2:
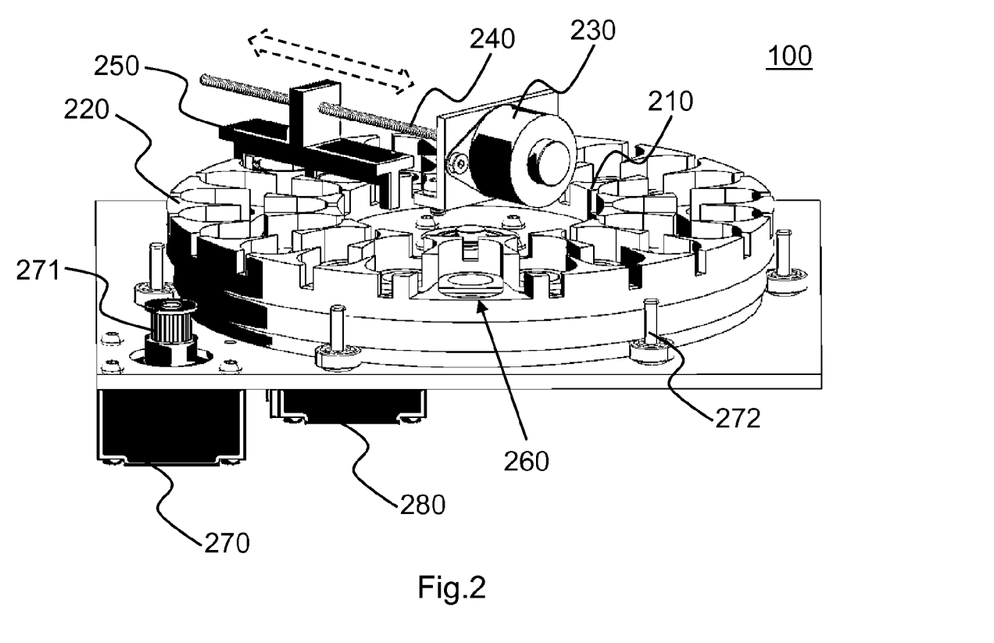
FIG. 2 shows a schematic picture of a filter module of an apparatus without a cover part according to an example embodiment of the invention.

FIG. 2 shows a schematic picture of a filter module 100 of an apparatus without a cover part according to an example embodiment of the invention. The filter module 100 may comprise at least two filter storages with a round shape, for example a circular shape. A first filter storage 210 is placed in the inner circle and may by default comprise the excitation filters, for example. A second filter storage 220 is placed in the outer circle and may by default comprise the emission filters, for example. The first and second filter storages may rotate in view of each other so that filters may be moved from the first storage to the second, and vice versa. The first and the second filter storages are rotated in view of each other for a desired position, where desired storage positions are opposite to each other. The filter transfer mechanism 120 may then move the filter from a filter storage position to another. Number of filter storage positions in each filter storage may depend on the size of the filter storages and the size of the filters. In an example embodiment of FIG. 2, the inner filter storage comprises 14 filter positions and the outer filter storage comprises 24 filter positions. One of the outer filter storage positions is a so-called exchange position 260 that can be used for adding or removing a filter.

In an embodiment, the first filter storage 210 may by comprise the excitation filters and the second filter storage 220 may comprise the emission filters. The filter module 100 may further comprise three or more filter storages placed in a similar way as described above.

In an embodiment, the filter transfer mechanism 120 may comprise a motor 230, a shaft 240 and a filter slide 250 for moving the filters between the filter storage positions. The motor 230 runs the shaft 240 that causes the filter slide 250 to move parallel (as shown by the arrow) to the shaft 240 and move the filters.

When the user of the apparatus 100 would like to add a new filter to the storage, the computer controlled system is activated. First, the user instructs the computer controlled system to trigger a filter load action. In the filter load action, the outer filter storage 220 is rotated so that the exchange position 260 is towards the user and matched to the exchange aperture 150 of the cover part. A new filter is placed to the exchange position 260 in the outer filter storage 220 and filter information is inputted to the computer controlled system by the user. The filter information may comprise any characteristics information, such as a bandpass wavelength, for example. After the filter information is inputted to the system, the filter transfer mechanism 230, 240, 250 and the rotating filter storages 210, 220 are configured to move the filter from the exchange position 260 in the outer filter storage 220 to any free filter position in the inner filter storage 210 or in the outer filter storage 220, for example. The outer filter storage 220 may be first rotated so that the exchange position 260 coincides with the filter slide 250 of the filter transfer mechanism. The rotation of the outer filter storage may be implemented using a motor 270, a driving wheel 271, running wheels 272 and a belt (not shown). The driving wheel 271 of the electronic motor 270 drives the belt around the outer filter storage 220. The belt rotates the running wheels 272 that drive the filter storage 220. At the same time, the inner filter storage 210 is rotated so that an empty filter position coincides with the filter slide 250. The inner filter storage 210 may be rotated using an electronic motor 280, in a similar way as for the outer filter storage 220. After the filter storages are rotated to desired positions, the filter transfer mechanics may move the filter from the outer filter storage position to the inner filter storage position. In case the inner filter storage would have been filled with filters, a filter from the inner filter storage would have been moved from the inner storage to the outer storage before adding the new filter to the system. The computer controlled system takes care that there are free filter positions in the storage to move filters between the inner and outer storages for carrying out the needed filter movements.

In an embodiment, the computer controlled system stores the filter information of all the filters to the system database. Furthermore, the system stores information of the exact filter storage position of all the filters in the storage. By doing this the system knows exactly which filter is in which filter storage position and when the user requests to use a desired filter for the excitation or the emission the computer controlled system may operate the apparatus to arrange the desired filter to the operating position in the filter storage.

Removal of a filter from the storage is done in a similar fashion but in reverse order. The removed filter is first moved to the inner storage 210 and the removed filter is rotated so that the filter coincides the filter slide 250. The outer filter storage 220 is rotated so that the exchange position 260 also coincides the filter slide 250. The removed filter is moved from the inner filter storage 210 to the exchange position 260 of the outer filter storage 220 and the outer filter storage 220 is rotated so that the exchange position coincides the exchange aperture 150. The user may then remove the filter from the aperture and at the same time the computer controlled system ensures removing the filter from the active set of filters in the apparatus 100.

In an embodiment, the user may select the desired filters to be used for measuring a sample from the computer controlled system database. The list of the filters may be provided and sorted for example based on the wavelength of the filters. Any of the filters in the filter storage may be used for both excitation purposes and emission purposes and the user does not need to know the exact position of the filter in the storage. The apparatus moves the user selected filters to correct positions. After moving the filters, the selected excitation filter coincides the excitation position in the excitation channel and the selected emission filter coincides the emission position in the emission channel. The user may also define a program of multiple filters to be used sequentially in the measurement. In such a case, the apparatus organizes the selected sequential filters in positions next to each other in the filter storage wheel. This kind of arrangement reduces the time needed for changing the filters.

In an embodiment, at least one of the excitation position and the emission position may be positioned outside the first filter storage and the second filter storage. A dedicated excitation/emission position (not shown) may be positioned for example radially next to the second filter storage 220, on the opposite side as the first filter storage 210. The filter transfer mechanism 230, 240, 250 may then move filters radially between the first filter storage 210, the second filter storage 220 and the dedicated excitation/emission position.

In an embodiment, the apparatus may also be configured to provide different sizes of focal points on the measured samples for the excitation and the emission lights, for example. The apparatus may comprise focal apertures of different sizes in the beam channel for this purpose. The different size apertures may be located in the inner or the outer filter storages or in the cover part of the apparatus. The used size of the focal aperture defines the size of the focal point on the sample. Using smaller size of focal point, a so-called cross-talk is reduced due the effect on the neighbor samples on the microtiter plate. A variety of different sizes of focal apertures may be implemented to the filter storage for enabling the desired size of the focal point.

Typically, in fluorescence polarization measurements, a polarization filter is required. In an embodiment, at least one filter position of the outer filter storage and at least one filter position of the inner filter storage comprise fixedly the polarization filters. These filter positions may be used for the fluorescence polarization measurements when inserting the desired excitation and emission filters to those positions. Thus, there is no need to insert separately a filter combination of the required wavelength filter and the polarization filter. Such filter storage positions may be used as normal storage position for any filter when not using the fluorescence polarization measurement.

In an embodiment, the filter storages may be placed on top of each other or beside each other. The filter transfer mechanism may move the filters between the filter storages in similar fashion as in inner/outer solution. In another embodiment the filter storage may comprise filter slides and a filter transfer mechanism in between for transferring the filters between the storage slide positions. In still another embodiment, the filter storage may comprise round-shape filter storage and slide filter storage with a filter transfer mechanism.

Figure 3:
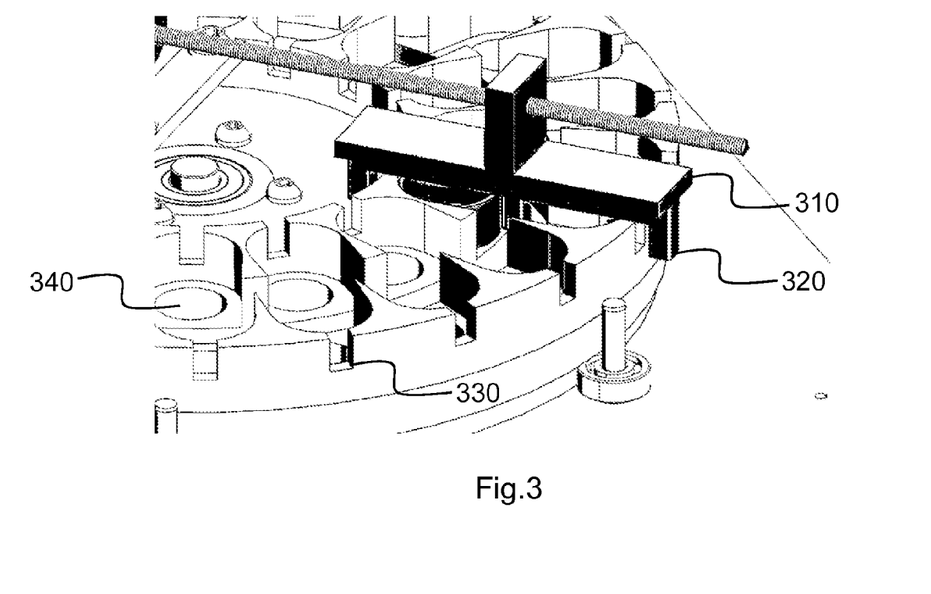
FIG. 3 shows a schematic picture of a filter module in a more detailed position for a filter transfer mechanism according to an example embodiment of the invention.

FIG. 3 shows a schematic picture of a filter module 100 in a more detailed position for a filter transfer mechanism according to an example embodiment of the invention. A filter slide 310 may comprise three fingers 320 for actuating the filters between the filter storage positions in the inner and the outer storages. Grooves 330 enabling the filter slide movement are located in both filter storages and also in the cover part (not shown) of the apparatus.

In an embodiment, at least one filter storage position comprises a focal aperture 340 to define the size of the focal point for the measured sample. All such filter storage positions that comprise the focal aperture 340 may be used as an operating position when positioned to the beam channel. The focal aperture 340 may also be located in the cover part of the apparatus.

Figure 4:
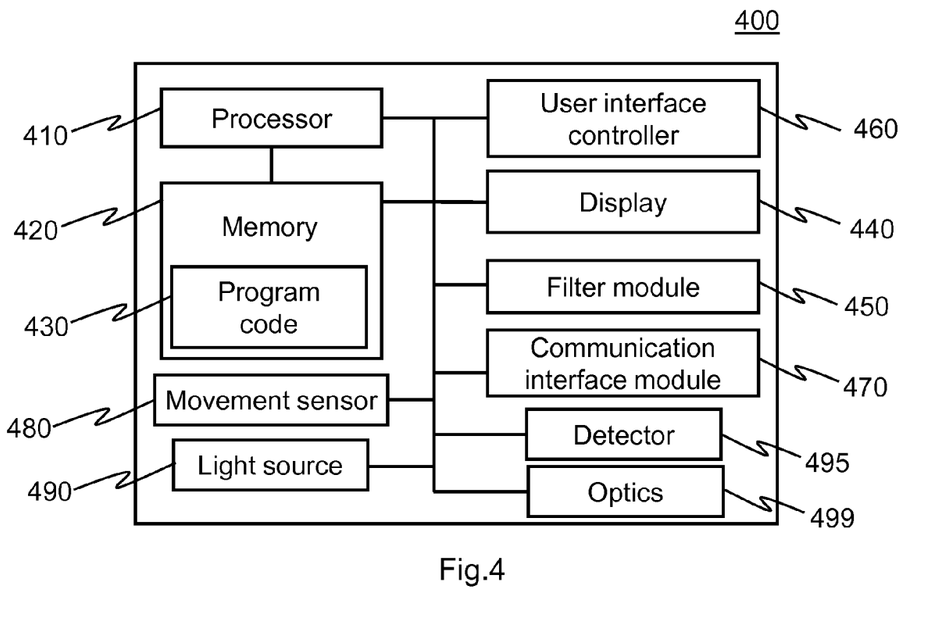
FIG. 4 presents an example block diagram of an apparatus in which various embodiments of the invention may be applied.

FIG. 4 presents an example block diagram of an apparatus 400 in which various embodiments of the invention may be applied. This may be a microtiter plate reader, an optical measurement apparatus or any similar apparatus.

The general structure of the apparatus 400 comprises a display 440, a filter module 450 with filter storages and a transfer mechanism, a communication interface 470, a movement sensor 480, a processor 410, and a memory 420 coupled to the processor 410. The apparatus 400 further comprises software 430 stored in the memory 420 and operable to be loaded into and executed in the processor 410. In some embodiments, the software 430 comprises one or more software modules and can be in the form of a computer program product. The apparatus 400 may further comprise a light source 490, a detector 495 and optics 499. The apparatus 400 may still further comprise a user interface controller 460 coupled to the processor 410.

The processor 410 may be, e.g., a central processing unit (CPU), a microprocessor, a digital signal processor (DSP), a graphics processing unit, or the like. FIG. 4 shows one processor 410, but in some embodiments the apparatus 400 comprises a plurality of processors.

The memory 420 may be for example a non-volatile or a volatile memory, such as a read-only memory (ROM), a programmable read-only memory (PROM), erasable programmable read-only memory (EPROM), a random-access memory (RAM), a flash memory, a data disk, an optical storage, a magnetic storage, a smart card, or the like. In some embodiments, the apparatus 400 comprises a plurality of memories. The memory 420 may be constructed as a part of the apparatus 400 or it may be inserted into a slot, port, or the like of the apparatus 400 by a user. The memory 420 may serve the sole purpose of storing data, or it may be constructed as a part of an apparatus serving other purposes, such as processing data.

The filter module 450 may comprise at least two filter storages and a filter transfer mechanism that all can be driven and controlled based on the program code 430 and the processor 410. The filter module 450 may also comprise dedicated excitation/emission positions outside the filter storages.

The movement sensor 480 may be included in the apparatus 400 for sensing the positions of the filter storages and the filter slide.

The communication interface module 470 implements at least part of the data transmission from the apparatus 400 to an external apparatus or system for various embodiments of the invention. The communication interface module 470 may be, e.g., a fixed interface module, such as a LAN, or a radio interface module, such as a WLAN, Bluetooth, GSM/GPRS, CDMA, WCDMA, or LTE (Long Term Evolution) radio module. The communication interface module 470 may be integrated into the apparatus 400 or into an adapter, card or the like that may be inserted into a suitable slot or port of the apparatus 400. The communication interface module 470 may support one radio interface technology or a plurality of technologies. FIG. 4 shows one communication interface module 470, but in some embodiments the apparatus 400 comprises a plurality of communication interface modules 470.

The display 440 may be for example a liquid crystal display (LCD) or a light-emitting diode (LED) based display. A touch-sensitive surface may be integrated to the display 440 as a touch display or a touch screen. The touch-sensitive surface may also be included as a separate element, for example as a touchpad.

The user interface controller 460 comprises circuitry for receiving input from a user of the apparatus 400, e.g., via a keyboard, graphical user interface shown on the display 440 of the apparatus 400, speech recognition circuitry, or an accessory device, such as a headset, and for providing output to the user via, e.g., a graphical user interface or a loudspeaker.

The light source 490 may be a polychromatic light source, such as a halogen lamp, for example. The optics 499 may comprise at least one lens that may be positioned between the light source 490 and a filter. The detector 495 may be a photoelectric detector, for example, converting light into an electrical signal for processing.

A skilled person appreciates that in addition to the elements shown in FIG. 4, in some embodiments the apparatus 400 comprises other elements, such as microphones, extra displays, as well as additional circuitry such as input/output (I/O) circuitry, memory chips, application-specific integrated circuits (ASIC), processing circuitry for specific purposes such as source coding/decoding circuitry, channel coding/decoding circuitry, ciphering/deciphering circuitry, and the like. Additionally, the apparatus 400 comprises a disposable or rechargeable battery (not shown) for powering the apparatus 400 if external power supply is not available. Another option is to use a capacitor instead of the battery for powering the apparatus 400 if external power supply is not available.

Figure 5:
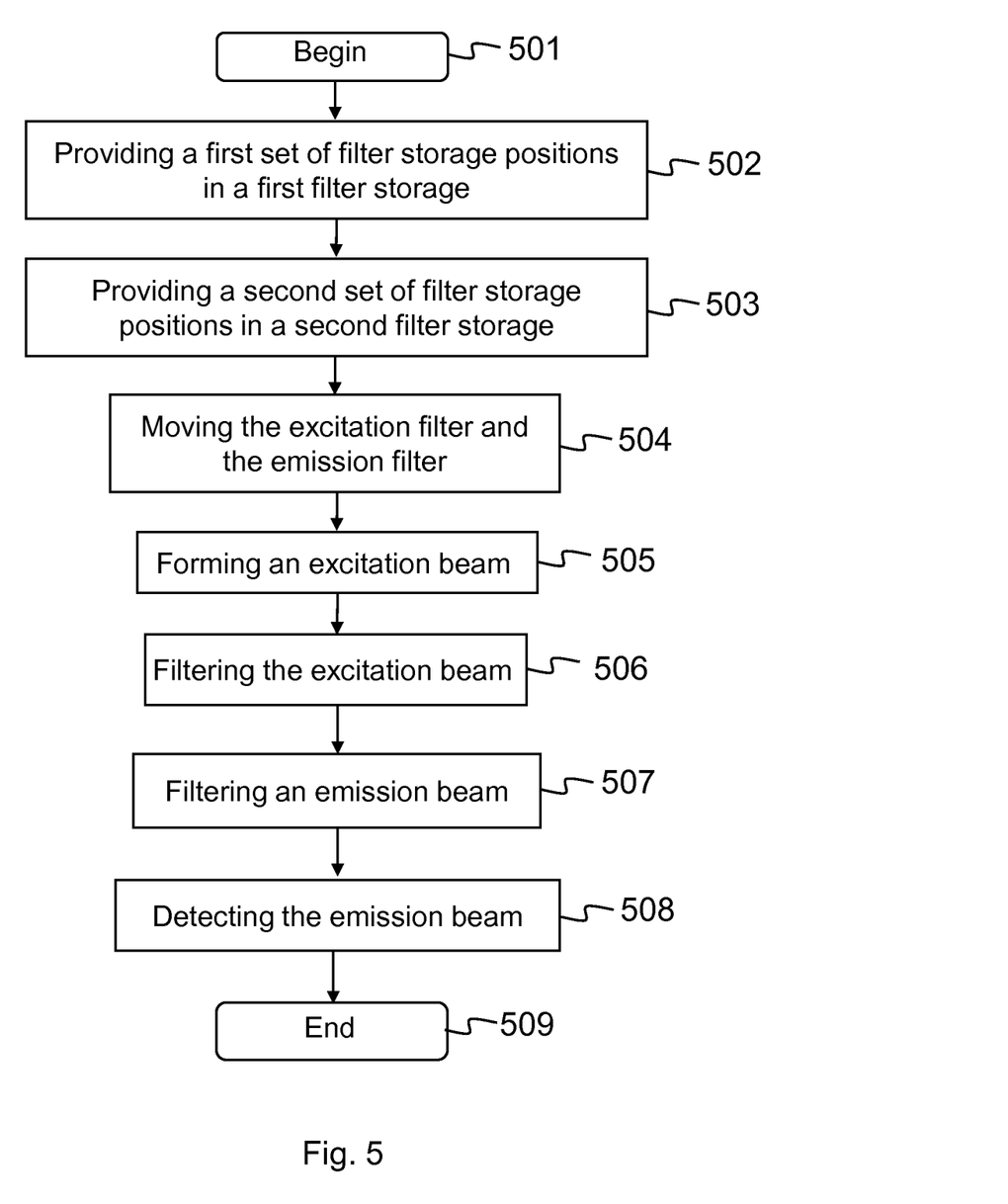
FIG. 5 shows a flow chart of a method in accordance with an example embodiment of the invention.

FIG. 5 shows an example flow chart of a method in accordance with an example embodiment of the invention. The method begins at block 501. In block 502, a first set of filter storage positions are provided in a first filter storage. A second set of filter storage positions are provided in block 503. In block 504 the excitation filter and the emission filter are moved between the excitation position, the emission position, the first set of filter storage positions and the second set of filter storage positions. In block 505, an excitation beam is formed. In block 506, the excitation beam is filtered. In block 507, an emission beam is filtered. The filtered emission beam is detected in block 508. The method ends at block 509. The example method presented in the foregoing is an example only. In other embodiments, different functions in the method may occur in a mutually different order.

Various embodiments have been presented. It should be appreciated that in this document, words comprise, include and contain are each used as open-ended expressions with no intended exclusivity.

The foregoing description has provided by way of non-limiting examples of particular implementations and embodiments of the invention a full and informative description of the best mode presently contemplated by the inventors for carrying out the invention. It is however clear to a person skilled in the art that the invention is not restricted to details of the embodiments presented above, but that it can be implemented in other embodiments using equivalent means or in different combinations of embodiments without deviating from the characteristics of the invention.

Furthermore, some of the features of the above-disclosed embodiments of this invention may be used to advantage without the corresponding use of other features. As such, the foregoing description shall be considered as merely illustrative of the principles of the present invention, and not in limitation thereof. Hence, the scope of the invention is only restricted by the appended patent claims.

The invention claimed is:

1. A filter module for storing and moving a filter between a filter storage position in the filter module, an excitation filter position in the filter module and an emission filter position in the filter module; the filter module comprising:
    a first filter storage comprising a first set of filter storage positions, at least one position of the first set of filter storage positions configured to be the excitation filter position overlapping at least partially an excitation channel of a microtiter plate reader apparatus;
    a second filter storage comprising a second set of filter storage positions, the second filter storage being disposed adjacent to the first filter storage, at least one position of the second set of filter storage positions configured to be the emission filter position overlapping at least partially an emission channel of the microtiter plate reader apparatus; and
    a filter transfer mechanism comprising a motor, a shaft and a filter slide, the motor configured to run the shaft to cause the filter slide to move, the filter transfer mechanism configured to move the filter between one or more of the excitation filter position, the emission filter position, a position in the first set of filter storage positions and a position in the second set of filter storage positions.

2. A microtiter plate reader apparatus for optically measuring samples, comprising:
    a radiation source configured to form an excitation beam in an excitation channel;
    a detector configured to detect an emission beam in an emission channel;
    a filter configured to be located in one of an excitation position in the excitation channel or in an emission position in the emission channel; and
    a filter module, the filter module comprising:
        a first filter storage comprising a first set of filter storage positions, at least one position of the first set of filter storage positions configured to be the excitation position, the excitation position overlapping at least partially an excitation channel of the microtiter plate reader apparatus;
        a second filter storage comprising a second set of filter storage positions, at least one position of the second set of filter storage positions configured to be the emission position, the emission position overlapping at least partially the emission channel of the microtiter plate reader apparatus; and
        a filter transfer mechanism comprising a motor, a shaft and a filter slide, the motor configured to run the shaft to cause the filter slide to move, the filter transfer mechanism configured to move the filter between one or more of the excitation position, the emission position, a position in the first set of filter storage positions and a position in the second set of filter storage positions.

3. The microtiter plate reader apparatus of claim 2, further comprising:
    at least one processor; and
        at least one memory including computer program code, the at least one memory and the computer program code being configured to, with the at least one processor, cause the apparatus at least to:
    store an association between optical information of the filter and a position of the filter, wherein the position of the filter being at least one of the following: the excitation position, the emission position, the first set of filter storage positions and the second set of filter storage positions.

4. The microtiter plate reader apparatus of claim 3, wherein the at least one memory and the computer program code being configured to, with the at least one processor, cause the apparatus further to:
    detect the movement of the filter caused by the filter transfer mechanism; and
    update the association between the optical information of the filter and the position of the filter.

5. The microtiter plate reader apparatus of claim 3, wherein the at least one memory and the computer program code being configured to, with the at least one processor, cause the apparatus further to:
    provide information on filters to a user of the apparatus;
    provide the user an option to select the filter for at least one of the following: the excitation position and the emission position; and
    move the filter, using the filter transfer mechanism, between the excitation position, the emission position, the first set of filter storage positions and the second set of filter storage positions, based on the user's selection.

6. The microtiter plate reader apparatus of claim 2, wherein the first filter storage and the second filter storage are positioned at least partially on the excitation channel and the emission channel, respectively.

7. The microtiter plate reader apparatus of claim 2, wherein the excitation position is configured to be a filter storage position of the first filter storage.

8. The microtiter plate reader apparatus of claim 2, wherein the emission position is configured to be a filter storage position of the second filter storage.

9. The microtiter plate reader apparatus of claim 2, wherein the second filter storage is configured to store an exchange filter position.

10. The microtiter plate reader apparatus of claim 9, wherein the filter transfer mechanism is further configured to move the filter between the exchange filter position and the first set of filter storage positions.

11. The microtiter plate reader apparatus of claim 2, wherein the first filter storage and the second filter storage are round-shaped.

12. The microtiter plate reader apparatus of claim 2, wherein the first filter storage and the second filter storage are slide-shaped.

13. The microtiter plate reader apparatus of claim 2, wherein the first filter storage and the second filter storage are configured to be movable compared to the radiation source and the detector.

14. The microtiter plate reader apparatus of claim 2, wherein the first filter storage is positioned next to the second filter storage.

15. The microtiter plate reader apparatus of claim 2, wherein at least one of the first set of filter storage positions and the second set of first filter storage positions comprises an aperture configured to provide a focal point to the measured sample.

16. The microtiter plate reader apparatus of claim 15, wherein at least two filter storage positions comprise apertures of different sizes configured to provide alternative focal points to the measured sample.

17. The microtiter plate reader apparatus of claim 2, wherein the apparatus comprises a microtiter plate reader and the measured samples are on a microtiter plate.

18. The microtiter plate reader apparatus of claim 2, wherein the sample is measured utilizing at least one of the following technologies:
    fluorescence intensity;
    absorbance;

luminescence;
time resolved fluorescence; and
fluorescence polarization.

19. A method for optically measuring samples, comprising:
providing a first set of filter storage positions in a first filter storage of a filter module, at least one position of the first set of filter storage positions configured to be an excitation position overlapping at least partially an excitation channel of an microtiter plate reader apparatus;
providing a second set of filter storage positions in a second filter storage of the filter module, the second filter storage being disposed adjacent to the first filter storage, at least one position of the second set of filter storage positions configured to be an emission position overlapping at least partially an emission channel of the microtiter plate reader apparatus;
moving a filter between one of the first set of filter storage positions and the excitation position using a filter transfer mechanism of the filter module;
moving the filter between one of the second set of filter storage positions and the emission position using the filter transfer mechanism of the filter module;
forming an excitation beam in an excitation channel using a radiation source;
filtering the excitation beam in the excitation channel using the filter as an excitation filter located in the excitation position;
filtering an emission beam in an emission channel using the filter as an emission filter located in the emission position; and
detecting the emission beam in the emission channel using a detector.

20. A computer program embodied on a computer readable non-transitory medium comprising computer executable program code which, when executed by at least one processor of a microtiter plate reader apparatus, causes the microtiter plate reader apparatus to perform the method of claim 19.

* * * * *